United States Patent [19]
Swenson

[11] Patent Number: 5,195,976
[45] Date of Patent: Mar. 23, 1993

[54] INTRAVENOUS FLUID TEMPERATURE REGULATION METHOD AND APPARATUS

[75] Inventor: Charles A. Swenson, Spring, Tex.

[73] Assignee: Houston Advanced Research Center, Houston, Tex.

[21] Appl. No.: 833,346

[22] Filed: Feb. 10, 1992

Related U.S. Application Data

[63] Continuation-in-part of Ser. No. 626,626, Dec. 12, 1990, Pat. No. 5,108,372.

[51] Int. Cl.⁵ .............................................. A61F 7/12
[52] U.S. Cl. ................................................... 604/113
[58] Field of Search ............... 604/113, 118, 121-123, 604/65-67, 151-153, 4; 128/DIG. 3, DIG. 12

[56] References Cited

U.S. PATENT DOCUMENTS

| | | | |
|---|---|---|---|
| 1,794,215 | 2/1931 | Titus . | |
| 2,124,293 | 1/1936 | Goldstein | 128/227 |
| 3,374,066 | 3/1968 | Farrant | 23/258.5 |
| 3,768,977 | 10/1973 | Brumfield et al. | 23/258.5 |
| 4,038,519 | 7/1977 | Foucras | 219/301 |
| 4,065,264 | 12/1977 | Lewin | 23/258.5 |
| 4,073,622 | 2/1978 | Luppi | 23/258.5 |
| 4,138,464 | 2/1979 | Lewin | 422/46 |
| 4,160,801 | 7/1979 | Bodolato et al. | 422/46 |
| 4,177,816 | 12/1979 | Torgeson | 128/400 |
| 4,231,425 | 11/1980 | Engstrom | 165/156 |
| 4,384,578 | 5/1983 | Winkler | 604/114 |
| 4,451,562 | 5/1984 | Elgas et al. | 435/2 |
| 4,464,563 | 8/1984 | Jewett | 219/298 |
| 4,525,163 | 6/1985 | Slavik et al. | 604/65 |
| 4,532,414 | 7/1985 | Shah et al. | 219/308 |
| 4,576,182 | 3/1986 | Normann | 128/692 |
| 4,585,056 | 4/1986 | Oscarsson | 165/133 |
| 4,612,170 | 9/1986 | Luther et al. | 422/46 |
| 4,622,140 | 11/1986 | Lee et al. | 210/177 |
| 4,623,333 | 11/1986 | Fried | 604/80 |
| 4,648,865 | 3/1987 | Aigner | 604/4 |
| 4,705,505 | 11/1987 | Fried | 604/80 |
| 4,707,587 | 11/1987 | Greenblatt | 604/113 X |
| 4,747,826 | 5/1988 | Sassano | 604/113 X |
| 4,874,359 | 10/1989 | White et al. | 604/113 X |

Primary Examiner—John D. Yasko
Attorney, Agent, or Firm—Gunn, Lee & Miller

[57] ABSTRACT

An apparatus for thermal regulation, or temperature control of intravenous fluid. The apparatus includes four subassemblies to control intravenous fluid temperature during rapid time varying fluctuations in fluid flow rates independent of ambient air temperature and initial fluid temperature. The first subassembly is an intravenous infusion subassembly containing a fluid reservoir, flexible tubing and a syringe for injecting fluid into a human. The second subassembly is a disposable heat exchange subassembly containing a wire heat exchanger and temperature and flow sensors. The heat exchanger is fabricated into the flexible tubing of the infusion subassembly. The third subassembly is a controller subassembly including a microprocessor system to control the heat exchange subassembly and power supplies. The fourth subassembly is the power supply subassembly which uses a variable voltage DC power supply to reduce low level 60 Hertz artifact signals that interfere with electronic monitoring systems such as the electrocardiogram.

25 Claims, 7 Drawing Sheets

INTRAVENOUS FLUID TEMPERATURE REGULATION METHOD AND APPARATUS

The following application is a continuation-in-part of application Ser. No. 07/626,626 filed on Dec. 12, 1990 now U.S. Pat. No. 5,108,372.

BACKGROUND OF THE INVENTION

A. Field of the Invention

The present invention relates to methods and apparatus for thermal regulation of artificially infused intravenous fluids.

B. The Prior Art

In surgery and after extreme trauma, patients receive intravenous fluids at high rates. Flow rates typically range between 40 and 2000 milliliters per hour and sometimes more. Typically, the fluid temperature upon entering the body is 20 degrees centigrade or cooler. Prior to infusion or transfusion the solutions are refrigerated to prevent incubation of harmful organisms in the fluid media. Upon infusion into the body, the intravenous fluid temperature increases to body temperature (37 degrees centigrade). The heat energy required for this essential temperature increase is supplied by an increased metabolic rate in the patient. This thermal load is not trivial when compared to normal metabolic processes in humans. As a baseline, 2000 food calories are consumed daily. This corresponds to a constant power consumption of 96.6 watts. Intravenous fluid, at twenty degrees centigrade, being infused at a rate of 2000 cubic centimeters per hour is equivalent to a thermal power load of 39.5 watts.

Thermal loading in this case is 41% of the baseline power consumption at 2000 food calories per day. Clearly, infusion induced thermal loading can be a principal contributor to the onset of thermal shock and possibly patient mortality. Additionally, such thermal loading may mask the onset of infection during early postoperative care. Presently there is no temperature control device in general widespread use in hospitals and trauma centers.

For purposes of this application the terms "intravenous fluid(s)" "IV solution" or "IV fluid" will be used interchangeably and will be used to generically refer to bodily fluids that may be infused or transfused into the body. Blood or blood components are the most typical form of such intravenous ("IV") fluid, however, the term should also be understood to refer to the multitude of artificial solutions or additives that are injected, infused or transfused into the arterial or venous system of patients during medical treatment.

An obvious method for heating an IV fluid is by placing the standard intravenous fluid bag into a warmer where the fluid would reach body temperatures and remain there with a high degree of stability. This method would be ideal if the intravenous fluid were not an ideal incubation media. However, such a preheating method would promote the growth of bacteria, fungi and other temperature sensitive organisms and is medically unacceptable.

Another method would be to employ a counterflow heat exchanger working on the principle of logarithmic mean temperature difference. This method would require a separate working fluid reservoir to be heated, a fluid pump, and a long heat exchanger. The method is not suitable for the rapid feedback required in a trauma center. Temperature control and flexibility are limited by the size of the working fluid reservoir. At best, the fluid reservoir size would equal the intravenous flow tube size. Even at this stage, a counterflow device is over complicated and poorly suited to the specified task. Additionally, this method does not satisfy the requirement of compactness and simplicity. The intravenous tubing could be run through a large waffle iron geometry heat exchanger. Such a device would work in the steady state flow mode with little feedback involved. However, rapid changes in flow rate and the need for precise control in the variable flow regime rule out this method. The waffle iron geometry would also be too large and time consuming in practice. The ideal heat exchanger must strongly couple the electrical input power directly to the intravenous fluid.

In designing the apparatus and method to effectively and efficiently regulate the temperature of IV fluids as they enter the human body certain engineering design parameters were developed and maintained. The device must not store a large amount of heat energy so that the feedback controls can rapidly adjust to variable fluid flow. Additionally, the heat exchanger had to be small and lightweight. Feedback sensors must monitor the flow rate, the initial fluid temperature, and the final intravenous fluid temperature before it enters the body. Any system must be able to detect a sudden flow shut-off. This prevents overheat in active feedback control systems and "tube" incubation in passive systems. A further constraint of an ideal system would be that the surface temperature of any heating element is maintained at or below 45° C. Red blood cells within the IV fluid which are exposed to temperatures above 45° C. may be damaged. Design of the heat exchanger should minimize "hot spots" along the length of any heating element for a given flow rate.

Prior art patents that have unsuccessfully addressed the identical problem include U.S. Pat. No. 1,794,215; U.S. Pat. No. 2,124,293; U.S. Pat. No. 4,038,519; and U.S. Pat. No. 4,384,578.

Specifically, in U.S. Pat. No. 1,794,215 to Titus a device for the intravenous injection of medicated solutions is disclosed. The device includes a heating device made of glass and shaped to provide a conduit through which the medicated solution flows. A heating element formed of materials such as copper wire is wound around the wall of the conduit. Surrounding the outer wall and in spaced relation thereto is an outer wall adapted to enclose the heating device throughout the major portion of its length.

U.S. Pat. No. 2,124,293 to Goldstein discloses an infusion apparatus for injecting fluids into the human body and more specifically a heating device therefor. The heating apparatus of Goldstein consists of an inner tube and a separate outer tube. The outer tube comprises a supporting tube of suitable material such as rubber, upon which a heating coil wound in the form of a helix is found. The heating coil is covered by a layer of heat insulated material such as asbestos which may in turn be covered by a rubber casing.

U.S. Pat. No. 4,038,519 to Foucras discloses a flexible heating tube for medical use. The heating tube includes a flexible pipe of transparent plastic material which is provided with at least one electrical helical resistance heating conductor and at least one helical filiform temperature measuring resistance probe. The two elements are wound on the same axis and are embedded in the wall of the flexible pipe and are surrounded in relationship to the bore of the pipe.

Finally, U.S. Pat. No. 4,384,578 to Winkler discloses a biomedical flow sensor which includes a resistor type heater on the upstream side of a metal contact shell used to heat a solution. Other patents identified as being of general interest include:

| | |
|---|---|
| 3,374,066 to Farrant | 4,525,163 to Slavik et al. |
| 3,768,977 to Brumfield et al. | 4,532,414 to Shah et al. |
| 4,065,264 to Lewin | 4,576,182 to Normann |
| 4,073,622 to Luppi | 4,585,056 to Oscarsson |
| 4,138,464 to Lewin | 4,612,170 to Luther et al. |
| 4,160,801 to Badolato et al. | 4,622,140 to Lee et al. |
| 4,177,816 to Torgeson | 4,623,333 to Fried |
| 4,231,425 to Engstrom | 4,648,865 to Aigrer |
| 4,451,562 to Elgas et al. | 4,705,505 to Fried |
| 4,464,563 to Jewett | |

As mentioned hereinabove, the apparatus and method of this invention have application in any medical or biomedical applications wherein an IV fluid is to be injected, transfused or otherwise artificially placed in the human body. Typical clinical situations in which the fluid heating apparatus of this invention will have specific utility are: trauma patients, patients in septic shock, patients with localized injuries, medical procedures wherein maintenance of basic metabolic rates are critical, and health care of compromised patients. In medical trauma the patient typically has a massive loss of blood, plasma and other body fluids. The patient is typically in shock and the patient's body temperature is typically already depressed. The shock is secondary to fluid volume depletion. It is important that any transfused fluids be incorporated into the body at body temperature to avoid a secondary shock caused by the temperature adjustment required by the body.

An example of septic shock is when a patient has peritonitis resulting from a ruptured internal organ. Typically an infection sets in and the body fluids "third space" meaning that the blood volume drops as plasma fluids swell the walls of the intestines and other abdominal organs. It is not uncommon that three to six liters of blood plasma can be lost. In replenishing the lost body fluids temperature maintenance of the fluids entering the body at close to normal body temperature is critical. Requiring metabolic adjustment of the internal body fluids may deepen trauma or cause other physiologically undesirable events to occur.

Localized injury is another example where plasma fluids swell the damaged area of the body. The fluid loss can be as much as 1.5 liters for a broken hip in the elderly or related types of injury. Lesser amounts are encountered with other injuries. The temperature sensitive replacement of body fluids in these trauma situations is critical.

It is important in many medical operational procedures to maintain the basic metabolic rate. A caloric food consumption of 2,000 food calories per day represents an average power consumption of 96.5 watts. In compromised patients body temperature can drop to 35.5°-34° C. or lower. If IV fluids are infused at 36° to 37° C. the body does not have to expend energy to warm the fluids. Energy can be used to fight infection or implement the restorative processes. Additionally, the infusion of cold fluids may actually cool patients. This effect could mask a temperature rise during the onset of severe infection and therefore delay critical treatment or medication.

Finally, the method and apparatus of this invention have shown utility in the treatment of compromised patients. Compromised patients are those patients described as the elderly, those with other diseases and metabolic problems, and immune compromised individuals such as aids patients, chemotherapy patients or radiation therapy patients; and finally, compromised patients include those with malignant diseases. The use of thermally sensitive materials and the transfusion of thermally sensitive materials is made possible through the use of the apparatus and method of this invention. The medical benefits vary from convenient to critical.

SUMMARY OF THE INVENTION

The apparatus or device embodying this invention incorporates four basic subassemblies into an integrated, functionally effective IV fluid temperature regulating device. The four subassemblies are an intravenous infusion assembly; a heat exchange assembly; a controller subassembly; and an energy source subassembly.

The first subassembly, the intravenous infusion assembly, may take any of a variety of well-known "sets". The most typical form of an intravenous infusion assembly involves a container or reservoir for fluid, flexible tubing connecting the fluid reservoir to the point of entry into the human; and a device such as a syringe for injecting the fluid into the human. Other well-known infusion assemblies can likewise be used. Examples of such assemblies would include "sets" of tubing, valves and other types of flow regulating devices that can be assembled to intravenously inject or pump one or more fluids or medications into the human body. A number of well-known devices are used to move the IV fluid along its intended path into the body. The devices range in sophistication from conventional gravity-feed devices to the complex IV infusion pumps that are now common in therapeutic settings. Also used are drop counting apparati that do not place a positive mechanical pressure on the fluid being fed intravenously.

The particular assembly of components of the intravenous infusion assembly is not limited in this invention. The only requirement is that a sufficient length of tubing be provided prior to entry of the fluid into the human body so that the temperature of the I.V. fluid can be regulated and/or monitored with the heat exchange assembly of this invention.

The second subassembly, the heat exchange assembly of this invention is mounted to or in the flexible tubing portion of the infusion assembly. The heating apparatus of this invention is adaptable for use with any of the known IV feed devices. The heat exchange assembly includes one or more heat exchangers; one or more fluid temperature sensors; one or more fluid flow sensors and a control signal wire bundle. The heat exchanger, which typically includes one or more twisted wire components, is extruded or embedded in the walls of the flexible tubing. The particular method or technique for achieving the embedding is a matter of choice to a person of ordinary skill in the art and may include an actual embedding of wire strands or the like into the plastic walls of flexible tubing followed by wrapping with a non-conductive material, i.e., shrink wrap. Other techniques may also be used.

The heat exchange assembly is mounted in a length of flexible tubing all of which is disposable. Standard electrical connectors are provided to connect the disposable heat exchanger (embedded in a section of flexible tubing) to the control signal wire bundle and ultimately to the controller subassembly.

The heat exchanger assembly and various fluid flow and temperature sensors are connected to the controller subassembly through the control signal wire bundle. The use of the control signal wire bundle enables the device of applicant's invention to be disposable and interchangeable with various intravenous infusion assemblies. The control signal wire bundle with the heat exchanger placed close to the human body enables temperature regulation immediately prior to an IV fluid entering the human body. Such placement minimizes a cooling or temperature gradient from existing between the heating apparatus and the body. The advantages of such temperature control have been detailed hereinbefore.

The third subassembly of this invention is a controller subassembly. The controller subassembly includes a micrprocessor based unit for logic control, and related input and output boards. The controller subassembly is functionally attached to the intravenous infusion assembly and to the heat exchange assembly such that the controller subassembly monitors and changes the temperature and mass flow characteristics of the IV fluid being pumped or gravimetrically flowing into the human body. In alternate embodiments of the invention the control signal wire bundle may be removably connected to the controller or removably connected to both the controller and one or more heat exchangers.

The fourth subassembly of this invention is the energy source. The energy source may be one or more electronic digitally programmable direct current power supplies. The energy source may also be either AC current, or simply battery power.

Note that this invention has utility with any of the well-known human bodily fluid injection devices. Typical of such applications are blood transfusions, kidney dialysis, and any other biomedical treatment that involve removal of fluid from the body, treatment of the fluid and return of the fluid or the injection of an artifical or substitute fluid into the body.

BRIEF DESCRIPTION OF THE DRAWINGS

Further details of the present invention are explained with the help of the attached drawings in which.

DESCRIPTION OF THE PREFERRED EMBODIMENTS

Figure 1A:
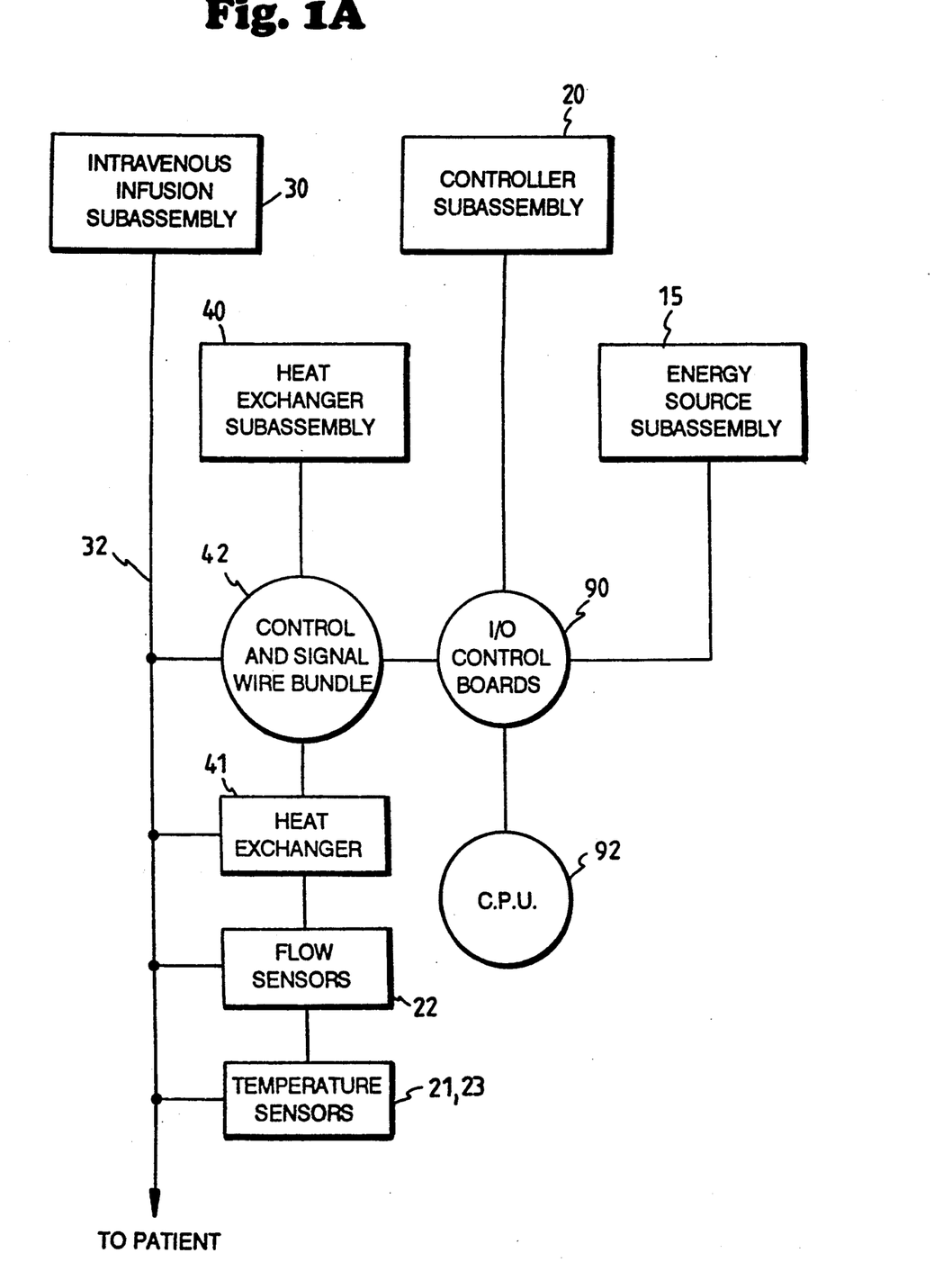
FIG. 1A shows the four subassemblies that comprise the apparatus of this invention.

FIG. 1A shows the four subassemblies that comprise the apparatus of this invention. The four subassemblies are: an intravenous infusion assembly 30; a heat exchanger assembly 40; a controller subassembly 20; and an energy source subassembly 15. Temperature control is performed by the heat exchanger subassembly 40 containing heat exchanger 41 which provides heat to IV tube 32, a component of the infusion subassembly 30. Flow sensors 22 and temperature sensors 21 and 23, also components of the heat exchanger subassembly 40, accurately measure IV fluid temperature and flow rate. The control and signal wire bundle 42 of the heat exchanger subassembly 40 carries signals from the flow sensors and to the heat exchanger from controller subassembly 20. Controller subassembly 20 contains a CPU 92 which sends and receives the signals through I/O control boards 90. The controller subassembly is independently powered and it controls the power supplies of energy source subassembly 15.

Figure 1B:
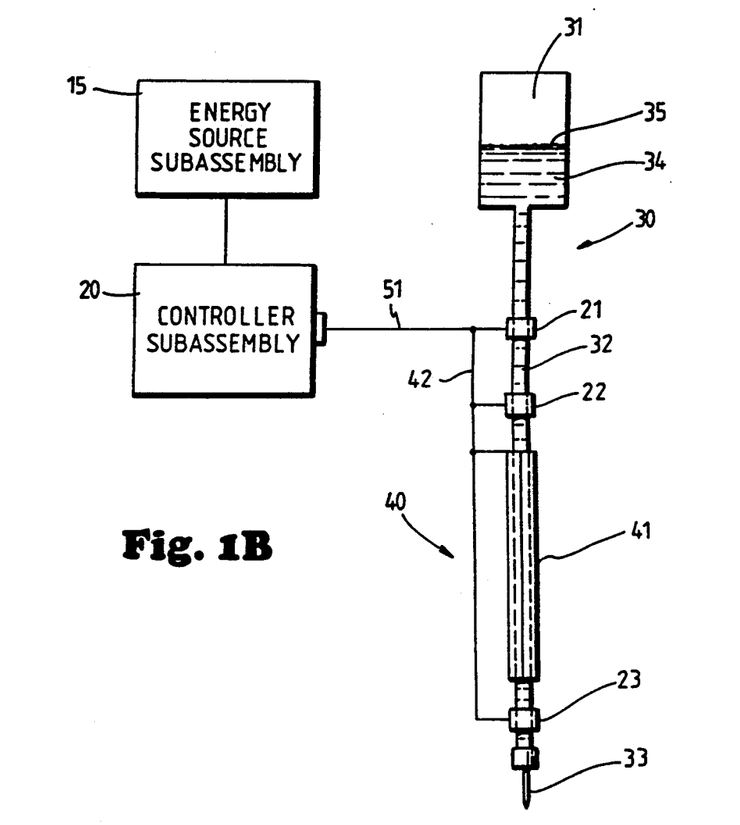
FIG. 1B is a schematic showing the four subassemblies with more detail of the heat exchanger subassembly and infusion subassembly.

Referring to FIG. 1B, more detail can be seen of the first subassembly, the infusion subassembly 30. The infusion subassembly 30, includes an IV bag 31, a clear flexible IV tube 32, and a hypodermic needle 33. The level of IV fluid 34 found in IV bag 31 is demonstrated numerically by the number 35. The components of the infusion subassembly 30 are all interconnected in standard medical hardware and connectors.

Also shown in more detail in FIG. 1B, the second subassembly, the heat exchange assembly 40, first contains the control signal wire bundle 42 running parallel to the IV tube 32 of the infusion assembly 30. One or more heat exchangers 41 are incorporated into the control signal wire bundle 42. These heat exchangers 41 are usually electrical resistors which are connected to control signal wires 42. A flow sensor 22 is also incorporated into the control signal wire bundle. Also included are initial 21 and final 23 temperature sensors. Both the temperature sensors 21 and 23 and the flow sensors 22 are connected to the control signal wire bundle 42. The control signal wire bundle 42 can be extended to encompass the wire harness 51 which connects to the controller subassembly 20, or the control signal wire bundle 42 can be removably connected to the wire harness 51 in close proximity to the intravenous infusion assembly 30.

Figure 3:
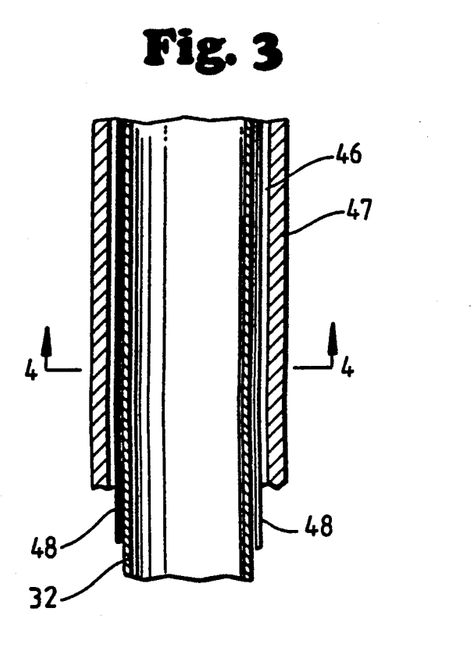
FIG. 3 shows a cut away view of wiring and insulating wrap for a heat exchanger.
Figure 4:
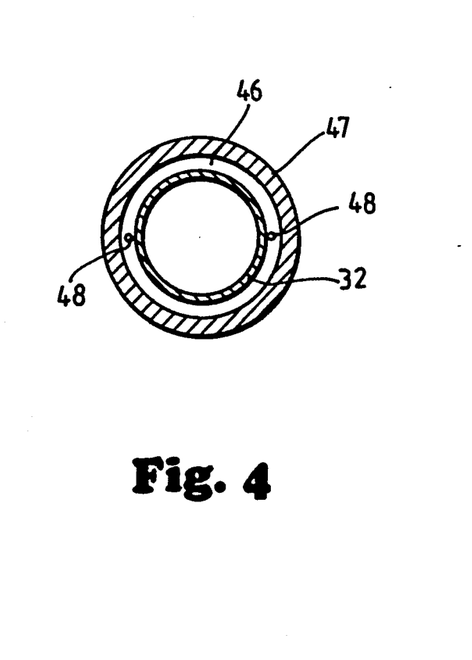
FIG. 4 shows a cross sectional view of the heat exchange assembly of FIG. 3.

Referring to FIG. 3 and cross sectional view in FIG. 4, the heater elements making up the heat exchanger can be either a multi-stranded heater wire 48 and/or an electrically conducting external skin 46 (For example a conducting plastic). Additionally these heater elements are located between the IV tube 32 and an electrically and/or thermally insulating outer skin 47.

Returning to FIG. 1B, the third subassembly, the controller subassembly 20, is equipped with two or more temperature monitoring channels, at least one flow monitoring channel, and at least one power output for the heat exchanger. The controller subassembly monitors the flow sensor 22.

Figure 2:
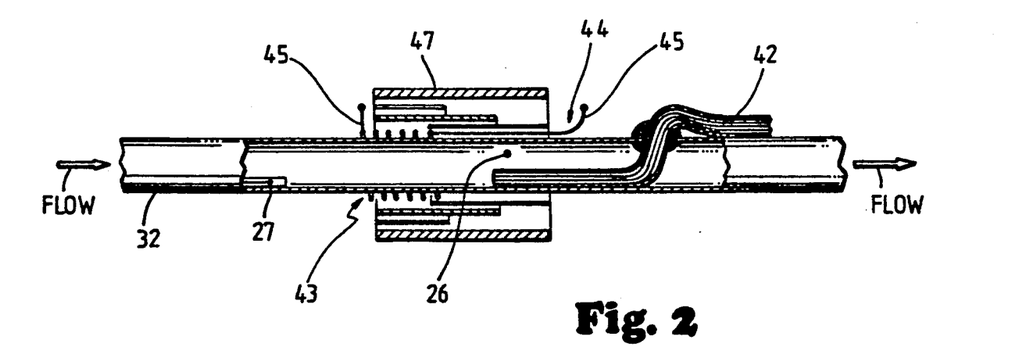
FIG. 2 shows one embodiment of the flow sensor of FIG. 1.

Referring to FIG. 2, the flow sensor 22 of FIG. 1B is a mass flow sensor which uses a flow sensor heater 43, and two temperature sensors: an upstream sensor 27, and a down stream temperature sensor 26. The sensors making up flow sensor 22 are monitored by the controller subassembly through the control signal wire bundle 42. There is an extension of the flow sensor heater 43, called a heater tail 44, which is in close proximity to the downstream temperature sensor 26. During steady state flow the IV fluid flow is roughly proportional to the inverse of the temperature difference across the flow sensor heater 43. The electrical power supplied to the flow sensor heater 43 is modulated in the time domain so that the temperature difference across the flow heater is modulated in the time domain so long as the IV fluid flows through the IV tube 32. When the fluid flow stops the heater tail 44 warms the downstream temperature sensor 26. The warming affect of the heater tail erases the temperature modulation signal and signals the no flow condition. Electrical heater leads 45 are interconnected to the control signal wire bundle 42.

Referring now to FIGS. 1B and 2, the primary component of the controller subassembly 20 is a microprocessor which is discussed later. One temperature input of the microprocessor monitors the final fluid temperature sensor 23. Two temperature sensor inputs and one power output constitute the mass flow sensor 22. The power to the flow sensor heater 43 is modulated in the time domain. The other power output is connected to the heat exchanger 41. The flow sensor 22 provides precise initial fluid temperature information and a signal which is proportional to the fluid flow. In practice, the flow rate signal is not exact because specific heat differs between the various intravenous fluids in use (blood plasma, saline, Ringers solution, various glucose solutions, Dudricts solution 1-2-3, other hyperalimentation solutions, and many others) and the effect of the external environment, i.e., air temperature and air currents over the exchanger.

The fourth subassembly of this invention is the energy source subassembly 15. The energy source subassembly may be one or more electronic digitally programmable direct current power supplies. The energy source subassembly may also be either AC current, or simply battery power.

Individual Components and Operation Descriptions

Individual components and precise operation of the components of the invention are described in more detail in sections which follow.

Heat Exchanger

The intravenous fluid heat exchanger 41 has two near optimal intravenous fluid heat exchanger geometries: a parallel wire heat exchanger and a coaxial heat exchanger. In either geometry, the power dissipated per linear cm should be no more than 2 watts. Depending upon the application, the length of a parallel wire heat exchanger length can be between 10 and 200 centimeters. The length depends upon the particular design for maximum intravenous fluid flow.

Referring to FIG. 3, FIG. 4 and FIG. 1B, the heat exchanger fabrication can be described as follows. The primary heat exchanger design is a parallel wire type. A clear intravenous tube 32, 1-4 mm diameter, is centered between two nichrome heater wires 48. The entire structure is encased in an insulating cylindrical sheath of 0.1-1 mm in thickness. The nichrome heater wires 48 are stranded to ensure flexibility of the heat exchanger 41. They are also bonded with an insulating glue to hold the wires together.

Measurements of this geometry with flow rates of 2400 milliliters per hour and an output temperature of 36 degrees centigrade indicate that about 75% of the input electrical power is transferred to the intravenous fluid 34. The heat exchanger 41 has a low mass for a minimum stored heat energy in the exchanger. All energy source subassembly 15 components are outside of the intravenous fluid volume for safety. The proper choice of materials allows the heat exchanger to be extremely flexible; the device can be bent 180 degrees in angle about a 3 centimeter radius during operation.

There are a variety of different fabrication methods for this exchanger type. A simple electrical winding pattern where the heater wire is composed of stranded wires 48. Series and parallel electrical winding configurations are used where the stranded heater wires 48 are twisted pairs to reduce AC noise coupling to heart rate monitors, and the like. The stranded heater wires 48 are connected at the end by an electrical jumper (not shown in drawing) to complete the simple winding pattern circuit.

A more typical geometry is the coaxial structure. A fine twisted pair heater wire insulated within a thin tube 0.1-1 mm in diameter and strung through the center of a standard intravenous tube 2-4 mm in inside diameter is used. This geometry is optimal in terms of thermal coupling efficiency and a low heat exchanger mass. Additionally, the coaxial heat exchanger is easily modeled since all heat energy is deposited into the intravenous fluid before radiating into the surrounding air. A clear insulating jacket (not shown in drawing) may be placed around the IV tube 32 to keep the IV fluid 34 warm between the heat exchanger and the patient.

An individual heat exchanger may define a uniform resistive, linearly tapered resistive, or exponentially tapered heater. For different flow rates, various configurations of coaxial heat exchangers will permit the blood to be warmed within the constraint that the heating element surface temperature not exceed 45° C. This may be accomplished using an exponentially tapered heating element when the surface temperature of the heating element is isothermal at a particular flow rate, initial fluid temperature, and air temperature. Design of such an element is governed by the following equation:

$$\left( Q[z] - \frac{T_1 - T_2}{\frac{\ln[D_2/D_1]}{2\pi k_v}} \right) = FC_p \left( \frac{dT_1}{dz} \right)$$

Where $Q[z]$ is the local power density. $T_1$ is the fluid temperature. $T_2$ is the air temperature. $D_2/D_1$ is the ratio of the tubing outside diameter over the tubing inside diameter. $F$ is the fluid flow. $C_p$ is the specific heat of the fluid. $z$ is the direction of length along the heat exchanger. The equation is more readable using $$\alpha = \frac{\ln[D_2/D_1]}{2\pi k_v} \; ; \; \Omega = FC_p.$$

$$\text{Yielding } Q[z] - \frac{T_1 - T_2}{\alpha} = \Omega \, T_1'$$

$Q[z]$ is the differential heat absorbed by the fluid. The $(T_1-T_2)/\alpha$ term represents the heat transfer between the environment and the IV tube. The $\Omega T_1'$ represents the differential heat trapped within the IV fluid that flows longitudinally along the length of the tube.

The equation can be further generalized by representing $Q(z)$ in terms of the fluid temperature $T_1$ and $T_H$ the local surface temperature of the heater elements. Specifically:

$$Q[z] = \frac{2\pi k_F (T_H - T_1)}{\ln[D_1/D_0]} = \gamma(T_H - T_1),$$

and

-continued $$\gamma = \frac{2\pi k_F}{\ln[D_1/D_0]}$$

The equation for the surface temperature of the heater element $T_H$ is $$T_H[z] = \frac{Q[z]}{\gamma} + T_1[z].$$

This equation can be solved by specifying either the heater power density function $Q[z]$ or the local surface temperature function of the heater element $T_H[z]$. Both forms are useful in the analysis and design of coaxial tube blood warmers.

The exponential taper in the power density is determined by taking the surface temperature of the heater to be an isotherm. The exponential power density is physically constructed by tapering the cross sectional area of the heater wire exponentially within the heater element.

The surface temperature constraint discussed above may also be met using a two-current isothermal heating element. In a particular refinement, the two-current isothermal warmer comprises a uniform heating element and an exponentially tapered heating element. In this refinement, the surface temperature of the insulating jacket surrounding the heating element would be uniquely isothermal, at maximum electrical current, for a particular flow rate, initial fluid temperature, and air temperature. Design of such an element is governed by the following equation:

$$T_1 = T_2 + I_1^2 \rho_A \alpha + I_2^2 \Delta\rho\left(\frac{\alpha}{1 - \alpha\beta\Omega}\right)\exp[-\beta z] +$$

$$\left(T_0 - T_2 - I_1^2\rho_A\alpha - I_2^2\Delta\rho\left(\frac{\alpha}{1-\alpha\beta\Omega}\right)\right) \times \exp\left[-\frac{z}{\alpha\Omega}\right]$$

Where:
$I_1$ is the current through the uniform heating element,
$I_2$ is the current through the exponentially tapered heating element,
$T_0$ is the initial fluid temperature (°C.),
$T_1$ is the fluid temperature (°C.),
$T_2$ is the air temperature (°C.),
$\rho_A$ is asymptotic linear resistivity,
$\Delta\rho$ is the amplitude term defining the change in resistance which is defined as the product coefficient of the exponential in the following equation:

$$Q[z] = Q_A[I_1] + \Delta Q[I_2]\exp[-\beta z] = I_1^2\rho_A + I_2^2\Delta\rho\exp[-\beta z]$$

Where $Q_A$ is the asymptotic power density. $\Delta Q$ is the change in power density, and $\beta$ is defined by, $$\beta = \frac{\gamma}{\Omega_D}\left(1 + \frac{1}{\alpha\gamma}\right)$$

Where $\Omega_D$ is generated from the design flow, and $$\gamma = \frac{2\pi k_F}{\ln[D_1/D_0]},$$

and $k_F$ is the thermal conductivity of the IV fluid in $$\left(\frac{\text{watts}}{\text{cm }°\text{C.}}\right).$$

Configurations for heating element assembly design using multiple isothermal warmers of the type described above can be used to meet the surface temperature constraint as well. The heating element assembly may, for instance, comprise two or more exponentially tapered heating elements arranged in series. A preferred embodiment for this configuration provides that the surface temperature of the insulating jacket surrounding each heating element, at maximum electrical current, is uniquely isothermal at a particular flow rate, initial fluid temperature, and air temperature.

Another exemplary configuration using multiple isothermal warmers provides for two or more two-current isothermal warmers of the type described above arranged in series. A preferred embodiment for this configuration provides that the surface temperature of the insulating jacket surrounding each heating element, at maximum electrical current, is uniquely isothermal at a particular flow rate, initial fluid temperature, and air temperature.

Still another exemplary configuration using multiple isothermal warmers provides for two or more exponentially tapered heating elements arranged in parallel. A preferred embodiment for this configuration provides that the surface temperature of the insulating jacket surrounding each heating element, at maximum electrical current, is uniquely isothermal at a particular flow rate, initial fluid temperature, and air temperature.

Yet another exemplary configuration using multiple isothermal warmers provides for two or more two-current isothermal warmers of the type described above arranged in parallel. A preferred embodiment for this configuration provides that the surface temperature of the insulating jacket surrounding each heating element, at maximum electrical current, is uniquely isothermal at a particular flow rate, initial fluid temperature, and air temperature.

Temperature Sensors

A mass flow sensor such as sensor 22 shown in FIGS. 1B and 2 requires that both the upperstream $T_0$ temperature sensor and the downstream $T_1$ temperature sensor be bathed in IV fluid. Other temperature sensors such as the final temperature sensor 26 can be placed outside the tube wall. The performance requirements for commercial embodiments of temperature sensors are that they must be accurate to ±0.1° C. and stable to ±0.03° C. The sensor must have a response time of 0.5 seconds, and dimensions no larger than 0.5 mm in diameter and 1 mm in length. Accuracy requirements are subject to medical review. Most sensor technologies (RTD, infrared, thermocouple, thermistor, black body radiation) can meet these requirements on a prototype basis. Mass production with this degree of reproducibility is rather easy for thermocouples because their signal is based upon differing Fermi voltages between dissimilar metals. Only the electronics or software need be calibrated. Other sensors may cost more to mass produce while satisfying these constraints. This issue will ultimately be resolved by the manufacturer.

Intravenous Fluid Flow Sensor

Fluid flow is measured by an electronic mass flow meter such as flow sensor 22 of FIG. 1B and FIG. 2. Along the fluid flow path, in the intravenous tube 32, a small 0-2 watt resistor is located between two thermocouple temperature sensors 26 and 27. The temperature difference between the two sensors is measured by a voltage comparison in the controller 20. This signal is inversely proportional to the mass flow and therefore the fluid flow rate. The geometry of the flow sensor heater resistor is most important. In reality, the heater is two resistors, a primary heater resister $R_1$, like flow sensor heater 43, and a secondary heater tail resistor $R_2$, like heater tail 44. 80-95% of the power is radiated in $R_1$. The secondary resistor is located within close proximity to the downstream temperature sensor $T_1$ like downstream temperature sensor 26. Spatially, the primary resistor is located a distance d (3-10 mm) upstream of the temperature sensor $T_1$. The sensor is located this far downstream to ensure that the fluid is sufficiently "mixed" to ensure a nearly linear temperature signal to flow relation over a flow range of 0-40 ml/min. The secondary heater tail resistor $R_2$ is used to sense flow cutoff. $R_1$ and $R_2$ are in series. The voltage modulation with the "heater-heater tail" geometry is to generate a different signal profile for the steady flow and no flow cases. During steady flow, and with nearly adiabatic flow changes, the $T_1$ temperature signal will oscillate slightly forming a temperature pulse train signal having a frequency nearly identical to the modulation frequency of the flow heater voltage. For mass flow sensors designed in this manner, the flow rate is proportional to the temperature difference over the average power. The flow signal fluctuates by about 5% about the mean value. The magnitude of the signal does not oscillate more about the mean because the flow sensors heat capacity has an averaging effect. The pulse train signal will continue so long as there is flow. When flow stops, $R_2$ the heater tail, which is in close proximity to the downstream temperature sensor $T_1$, warms the $T_1$ sensor and removes the modulated pulse train signal. The no flow signal condition can be resolved within two periods of flow sensor modulation, this corresponds to 1-3 seconds. The response and accuracy of this type sensor can be enhanced by further miniaturization.

The important components of flow sensor 22 are: The primary flow heater 43, which is a nichrome wire coil wrapped around the IV tube 32. The heater tail 44, which is an extension of the nichrome wire that runs along the outside of the tube and parallel to the axis to the tube. The distance of the downstream temperature sensor 26 $T_1$ to the flow heater coil 43 should be between 3 and 9 mm. Additionally, the temperature sensor 26 $T_1$ is within proximity of the heater tail 44, but it is located on the opposite side of the tube to avoid direct conductive wall heating of the $T_1$ sensor during the steady flow condition. The heat shrink tubing surrounding the temperature sensor $T_1$ acts like a spring to hold the sensor on the other side of the tube wall. For the mass flow sensor, it is extremely important that both temperature sensors are in intimate contact with the IV fluid. Two temperature sensors are required to avoid any introduction of an integrated error as the initial temperature of the IV fluid, $T_1$, may change with time. The heater-tail geometry can also be manufactured using a variable conductor density heater tape that can be applied to the outside of the IV tubing.

Figure 5:
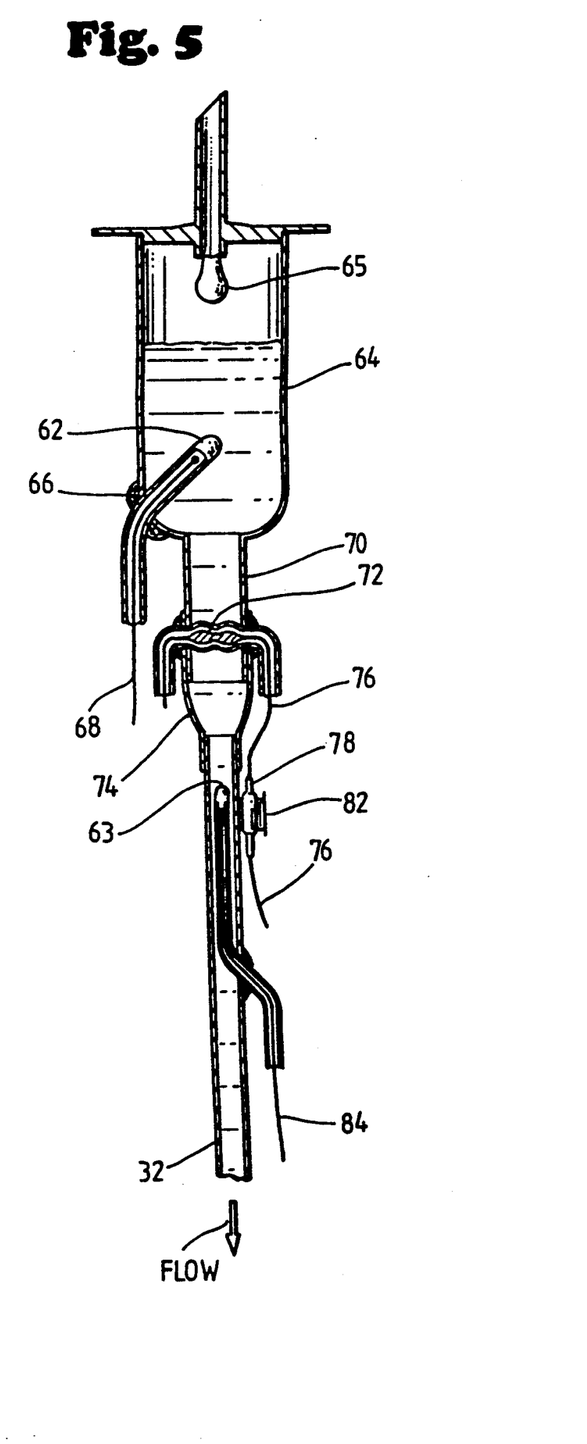
FIG. 5 shows an alternate embodiment of the flow senser used in the present invention.

FIG. 5 shows an alternate configuration for the mass flow sensor. The initial $T_0$ temperature sensor 62 is inserted in a hole through a standard IV drop counting glass 64. IV fluid 65 is shown dropping into the IV drop counting glass 64. The hole for the $T_0$ temperature sensor 62 is sealed by a clear PVC-CPVC cement seal 66. Thermocouple signal wire 68 carries a signal from $T_0$ temperature sensor 62 to the controller subassembly via the control signal wire bundle (not shown). IV drop counting glass 64 is connected to a clear 5/16 PVC tube (thermal mixing chamber 70) where the electrically isolated flow heater resistor 72 is located. The electrically isolated flow heater resistor 72 is electrically connected in series with a second resistor, the heater tail resistor 78, via a flow sensor heater lead 76. The heater tail resistor 78 is attached to the outside of the IV tube 32 by a Kapton tape heater tail clamp 82. The thermal mixing chamber 70 is connected to standard IV tubing 32 via a clear heat shrink transition 74. A downstream $T_1$ temperature sensor 63 is located inside the IV tube 32 and in close proximity to the heater tail resistor 78. The downstream $T_1$ temperature sensor signal wires 84 and the flow sensor heater leads 76 are attached along with thermocouple signal wires 68 as a group to the control signal wire bundle (not shown).

Other possible fluid flow sensing methods are high frequency flow meters, magnetic flow sensors, simple rotary flow sensors, pressure difference sensors, and drop counters. The controller can also function using flow feedback signals from a flow control device. A detailed analysis of cost and applicability must be done before these other flow measurement techniques can be considered for adoption. An additional analysis of its cost in comparison to the mass flow rate method must also be done. For the time being, electronic mass flow rate meters work and are simpler in terms of fabrication and principle of operation. This does not mean that these other measurement techniques should be excluded from any design.

Control Signal Wire Bundle

The control signal wire bundle is connected through standard electrical connectors to the disposable heat exchanger. The control signal wire bundle is connected at the other end to the controller subassembly. The control signal wire bundle may be electrically conductive cable strands, or optical fibers. The control signal wire bundle carries signals from the heat exchanger assembly and various fluid flow and temperature sensors to the controller subassembly. The use of the control signal wire bundle enables applicant's invention to be disposable and interchangeable with various intravenous infusion assemblies.

Operation Process

Referring to FIG. 1B, the process of operation of the invention can be described as follows. The IV tubing 32 is filled with fluid 34 and purged of air; then flow is established. The control wire harness 51 is plugged into the controller 20. The controller 20 is then switched on. A flow signal is recorded by the controller 20 and the appropriate amount of electrical power 15 is metered to the heat exchanger 41 using the relation:

$$P = (T_{set} - T_0) C_s \frac{F}{\epsilon} - a\dot{T}_2$$

Where $T_{set}$ is the set point temperature (say 36° C.), $T_0$ is the initial fluid temperature in °C., $C_s$ is the heat capacity of the IV solution (say 4.18 $joules$/ml°C.), F is the IV fluid flow in (ml/sec), $\epsilon$ is the working efficiency of the heat exchanger, $\dot{T}_2$ is the time derivative of the final temperature $T_2$, and $a$ is an empirical damping coefficient.

The electrical power sent to the heat exchanger is updated cyclically within a logical control loop. Each time the microprocessor 20 cycles through this loop, the flow is updated and the working efficiency is recursively calculated based upon a flow weighted bisection method.

The recursive efficiency is given by $$\epsilon_n = \left[ \frac{\epsilon_{n-1} + \left(\frac{P_{out}}{P_{n-1}}\right)\frac{F}{w}}{1 + \frac{F}{w}} \right]$$

$\epsilon_n$ is the updated efficiency. $\epsilon_{n-1}$ is the old efficiency. $P_{n-1}$ is the applied power during the last loop cycle. w is a weighting factor related to the cycle frequency of the microprocessor. $P_{out}$ is the amount of electrical power that actually heats the fluid. $P_{out}$ is given by $$P_{out} = (T_2 - T_0) C_s F.$$

The initial working efficiency of the exchanger is chosen between 20% and 90% depending linearly upon the flow signal. The physical efficiency is between 20% and 75%. Efficiency is proportional to the power applied to the heat exchanger. (The wires get hotter.)

This control loop is repeated until one of the following conditions occur: 1) Flow stops. 2) the magnitude of the time derivative of the flow exceeds a specified value. 3) The final temperature of the fluid, $T_2$, is greater than an assigned value (39° C.). 4) There is an error signal indicating that one or more of the control signal lines is not working. 5) A periodic reset occurs after the controller runs for a moment of time (1 hr.). Error conditions (1-4) cause the controller 20 to shut down. Condition (5) results in the device shutting down for 1-5 min. After which time the controller starts anew.

Summary of Controller Block Diagram

Figure 6:
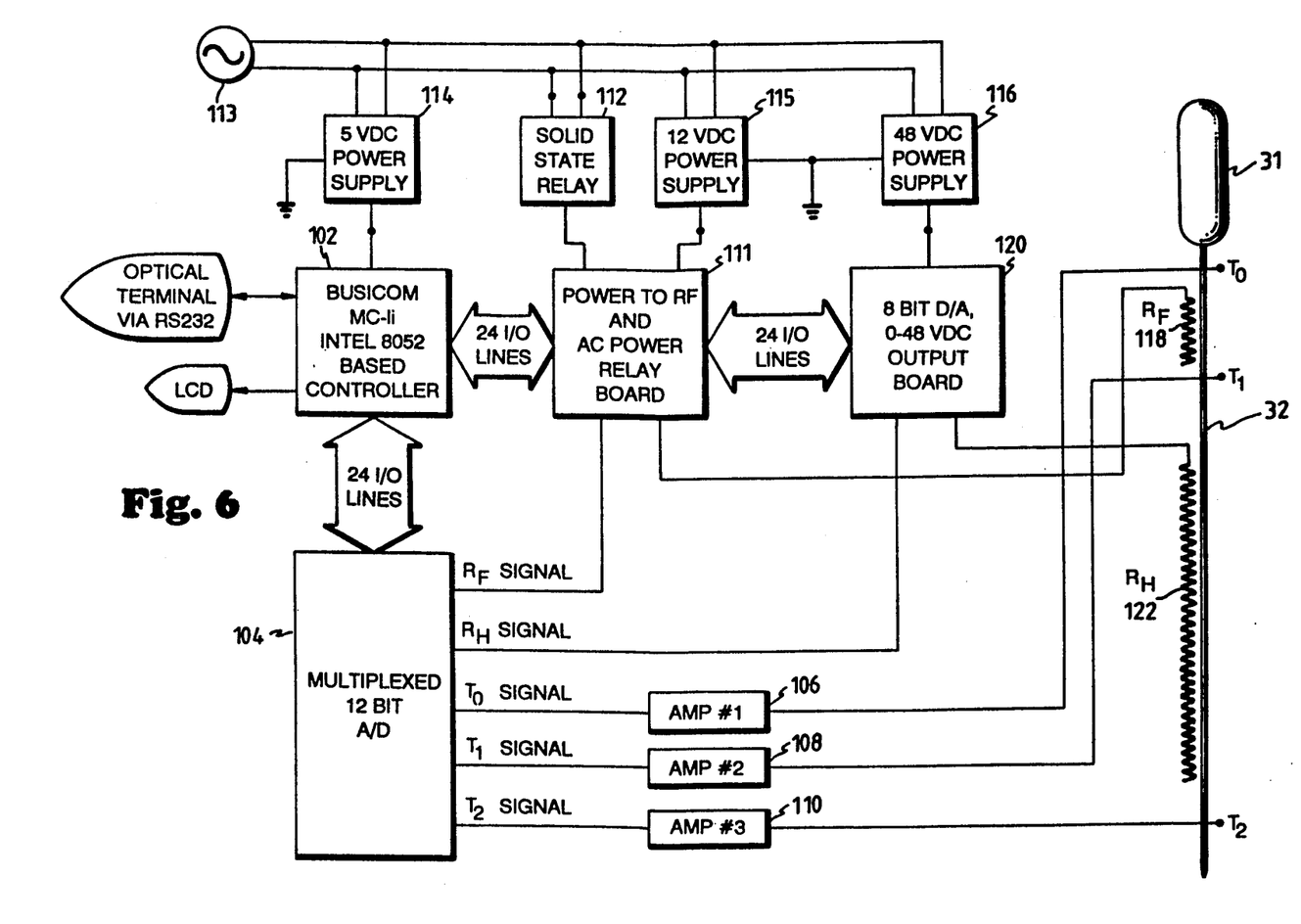
FIG. 6 is a schematic representation of the control logic circuitry of the controller.

FIG. 6 is a block diagram for the controller used in the present invention. In addition to the controller components, FIG. 6 for reference also shows the heat exchanger resistor $R_H$, flow heater resistor $R_F$, thermocouple contacts $T_0$, $T_1$, $T_2$, the IV tube 32, IV bag 31, and AC and DC power supplies.

The controller unit is based upon the Basicon MC-li microcontroller 102. Basicon, Inc. is a company located in Portland, Oreg. The controller's CPU is an Intel 8052 microprocessor configured to have a memory of a 16 kilobytes, an 8 kilobyte eprom, and six I/O ports from two Intel 8255 programmable peripheral interface chips. This configuration is stock and was purchased from Basicon. The multiplexed 12 bit A/D board 104 was also purchased from this company.

Three thermocouple signal processors 106, 108, and 110 are used to amplify and linearize the voltage signals from the thermocouple sensors received at points $T_0$, $T_1$ and $T_2$. These are stock items purchased from OMEGA Corporation in Massachusetts, (Model TAC-386-JF).

The "Power to $R_F$ and AC Power Relay Board" 111 is a unique construction. This board has three functions: 1) An output line is connected to a solid state relay 112 which controls AC power 113 to a 12 volt power supply 115 and 48 volt power supply 116. If an error condition occurs in the microprocessor the electrical power to the IV device can be cut off at the source. The relay is turned off when the controller is switched on. 2) The board also contains a switching buffer for the modulated flow sensor heater signal coming from the microcontroller. 3) The voltage signal across a shunt resistor (0.5-2 ohm) which is in series with the flow heater resistor $R_F$ 118 is connected to one of the 12 bit A/D board channels to monitor the flow heater circuit. All components on this board, the solid state relay and AC and DC power supplies are made from available parts.

The "8 bit D/A, 0-48 VDC output board" 120 is also a unique construction. It has an 8 bit microprocessor interface to a D/A chip. The board has two functions: 1) The DAC chip's voltage output is amplified using a power transistor follower circuit to control the current in the heat exchanger resistor $R_H$ 122. 2) The voltage signal across a shunt resistor (0.5-2 ohm) which is in series with the heat exchanger resistor $R_H$ 122 is also sent to the 12 bit A/D board for circuit status checking by the microcontroller. Components on this board are commercially available parts.

Note again that shunt resistor voltage signals can be used to measure the resistance of $R_F$ and $R_H$. The specific values of either shunt resistance is programmed into software so that one controller can identify and work with many different disposable heat exchanger configurations.

Controller Operation Flow Chart

Figure 7:
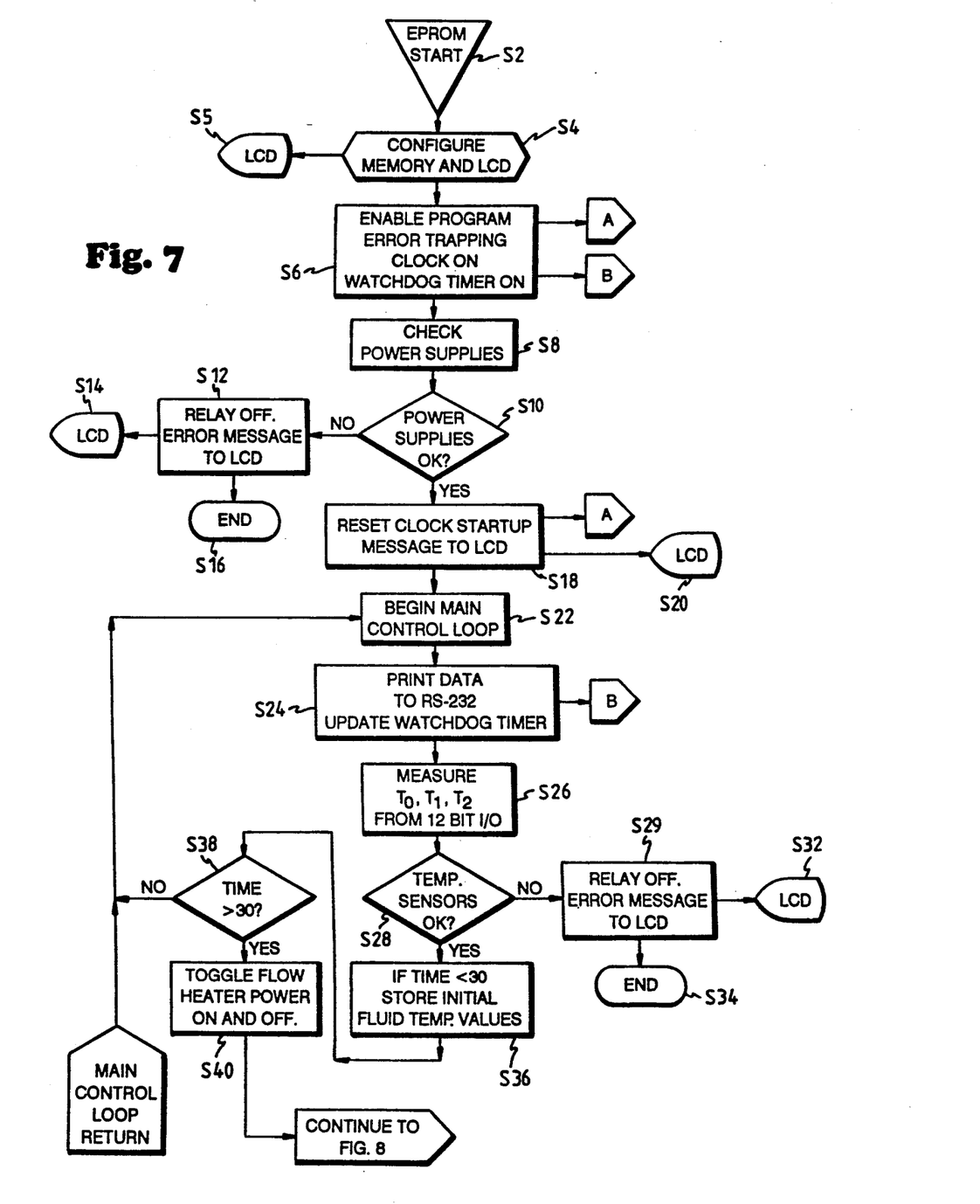
FIGS. 7-10 are flow charts showing the program operation steps performed in the controller subassembly microcomputer.

FIG. 7 shows the initial steps performed by the controller software. Upon turn on the microprocessor in step 1 (S1) within the controller subassembly, the microprocessor begins executing a program which is stored on an eprom chip on the CPU board. The program then configures the input output memory address locations in step 4 (S4) and sends a series of startup instructions to the LCD screen driver hardware in S5.

In S6 software error trapping flags are then set so that the CPU executes a shutoff in the event of software failure. The 8052 microprocessor is equipped with an internal watchdog timer also set in S6. An internal watchdog timer, which is also set in S6, is a subprogram that is executed simultaneously with the main program and is called at subroutine flags A or B.

Figure 9:
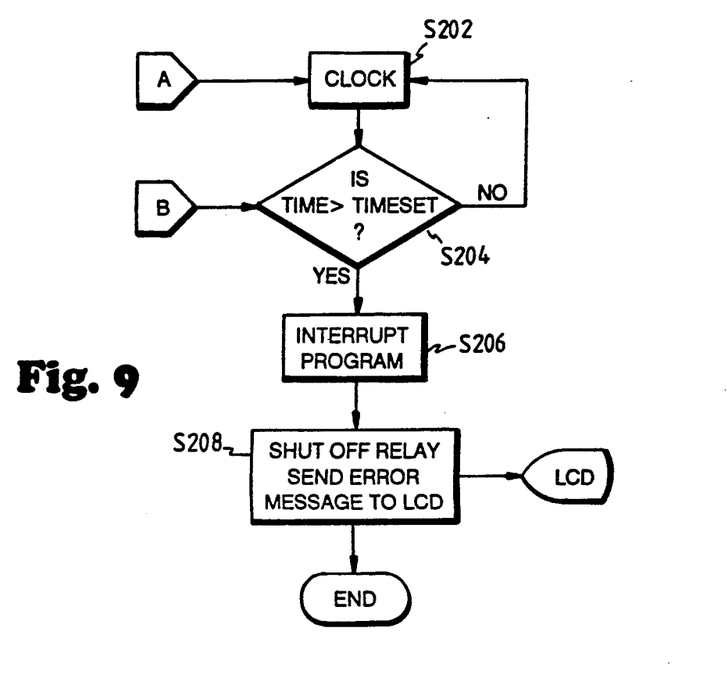

FIG. 9 shows the steps of execution of the auxiliary watchdog timer. The watchdog monitors the clock in S202 and checks to see if the clock time has exceeded the value of a time set variable set by the main program. If the clock time exceeds the time set value in S204 the watchdog process interrupts the main program and a specified device shutoff is executed by the microprocessor in S208. If the program is running properly the time set variable is updated periodically. External watchdog timers are also installed to provide another level of error protection.

Returning to FIG. 7, the program the checks the circuit integrity of the 12 and 48 volt power supplies within the energy source subassembly in S8. This is accomplished by measuring the voltage across shunt resistors in series with each power supply. These voltage signals are digitized using the 12 bit analog to digital converter. If either power supply circuit fails, as indicated by S10, the program then executes a controlled shutdown in S12. Power is cut off from the energy source subassembly 20 by opening the solid state relay. Then an error message is sent to the LCD screen in S14. Program execution is then terminated in step 16 (S16).

If the power supplies are working properly the internal clock is reset and started again in S18 which calls a subroutine at flag A. A startup message is then sent to the LCD screen in S20.

The program then begins the main control loop in S22. At the beginning of the control loop in S24 diagnostic data is sent to the RS-232 serial data port where an external interactive terminal device can be optionally connected. The time set variable for the watchdog timer is then updated and called at subroutine flag B. This is the only point in the loop where the time set variable is reset.

Next in S26 the temperature signals $T_0$, $T_1$, and $T_2$ are digitized using the 12 bit analog to digital (A/D) converter. The $T_0$, $T_1$, and $T_2$ temperatures correspond to the following respective locations: the initial temperature sensor 21, the downstream temperature sensor 26, which is within the flow sensor 22, and the final temperature sensor 23. If any temperature sensor fails to properly function, as determined in S28, the program in S29 opens the solid state relay, sends an error message to the LCD in S32, and terminates execution in S34.

If time<30 seconds in S36 the $T_0$, $T_1$, and $T_2$ values are stored in separate data registers (say T00, T10, and T20) which represent the initial temperatures of the IV fluid solution. These temperature values are used to compensate for any thermocouple amplifier signal drift in the calculation of flow.

If time<30 seconds, as determined in S38, the main control loop ends here and the program returns to the beginning of the main control loop. Otherwise the control loop continues.

After 30 seconds the electrical power to the flow sensor heater $R_F$ is modulated by toggling the power cycle to cycle in S40. The pattern is that the power is on one loop cycle and off the next. This is a 50% modulation.

Figure 8:
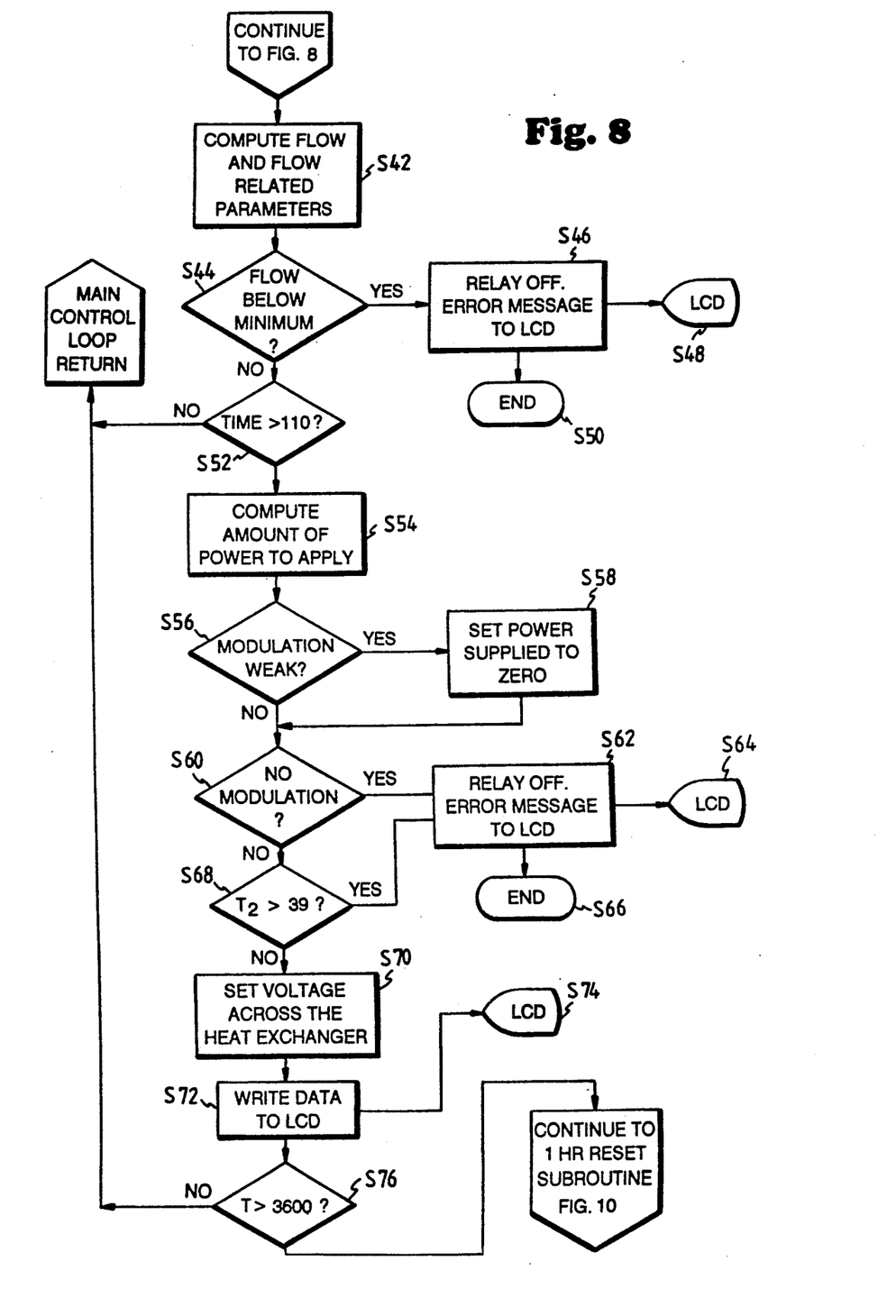

Continuing the program in FIG. 8, the flow, flow time derivative, and the modulation are then computed logically from the temperature signals in S42. The modulation of the temperature signal across the flow sensor heater 43 is measured by comparing sign of the time derivative of the temperature $T_1$ from cycle to cycle. If $T_1$ changes sign from cycle to cycle the signal modulation is good and nearly steady flow is present. If flow stops or decreases rapidly the heater tail resistor 43, which is in close proximity to the downstream temperature sensor 26 $T_1$, warms the $T_1$ sensor thereby erasing the modulation signal and providing a no flow signature that the microprocessor can recognize.

80 seconds is allowed for the flow sensor to warm up. If the sensor gets too hot during this time (as determined in S44 as the result of no flow) the program executes a shutdown in S46 by opening the solid state relay, sending an error message to the LCD in S48 and terminating execution in S50.

If time<110 seconds the main control loop ends and the program returns to the beginning of the main control loop in S52. Otherwise the control loop continues.

The power to be applied to the main heat exchanger is logically computed based upon the temperature and flow conditions in S54. The algorithm used is a temperature dampened proportional flow bisection algorithm. The rate of convergence of the working efficiency is changed based upon the flow rate and the temperature difference between then set point temperature and the IV fluid exit temperature $T_2$. All these various methods use a bisection technique to determine the working efficiency.

If the modulation signal is weak as determined in S56, meaning that the sign of the time derivative of $T_1$ has not changed from the last cycle, the power to be applied is set to zero in S58.

If there is no modulation signal for four cycles, as determined in S60, the program executes a shutdown in S62 by opening the solid state relay, sending an error message to the LCD in S64, and terminating execution in S66 under the assumption that there is no flow present.

If the exit temperature of the IV fluid $T_2$ is too hot (39 degrees centigrade as determined in S68) the program executes a shutdown by opening the solid state relay, sending an error message to the LCD, and terminating execution.

If all the tests for temperature, the flow, and circuit integrity are passed the CPU logically assumes that the device is functioning properly and then sends a digital signal to the digitally programmable power supply that adjusts the voltage across the heat exchanger in S70. The combination of the 48 volt direct current power supply and the 8 bit digital to analog output board comprise the digitally programmable DC power supply in the present working example.

In S72, The output temperature $T_2$, flow and modulation information are written to the LCD screen of S74 as status information.

Figure 10:
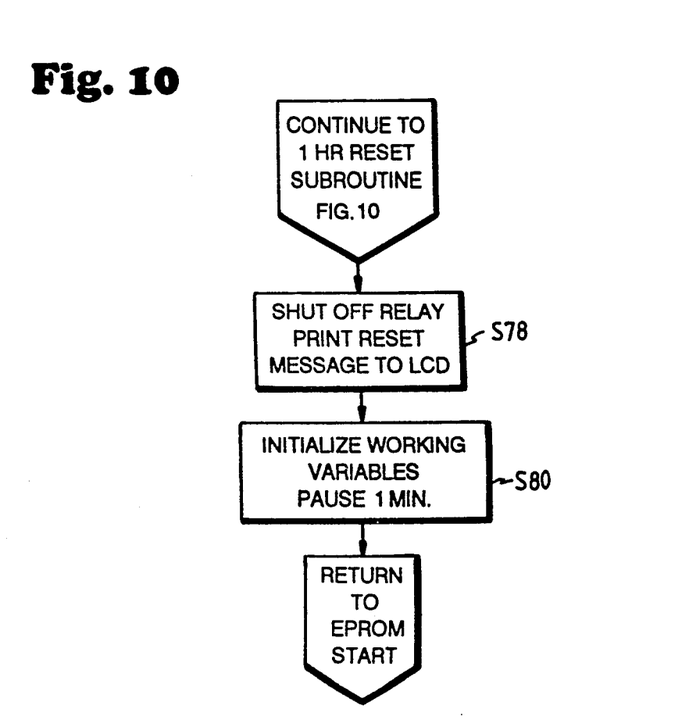

The main control loop ends here. If time<3600 seconds, as determined in S76, the program returns to the beginning of the main control loop. Otherwise a 1 hour reset subroutine of FIG. 10 is executed so that power to the heat exchanger and the flow sensor is cutoff in S78 allowing the flow sensor to cool for one minute in S80. This is done to prevent any integrated drift in the thermocouple signal amplifiers from erroneously affecting the flow calculation. Finally, control is returned to the eprom startup of FIG. 7 after the one minute delay is complete.

Although the invention has been described above with particularity, this was merely to teach one of ordinary skill in the art how to make and use the invention. Many modifications will fall within the scope of the invention, as that scope is defined by the following claims.

What is claimed is:

1. A device for controlling the temperature of intravenous fluids as they enter the human body comprising:
   (a) an intravenous infusion assembly;
   (b) a heat exchange assembly removably mounted to said intravenous infusion assembly, wherein said heat exchange assembly comprises:
      (i) one or more heat exchangers coaxially mounted within said intra venous infusion assembly;
      (ii) one or more fluid temperature sensors;
      (iii) one or more fluid flow sensors; and (iv) a control signal wire bundle;
(c) a controller, said controller being functionally attached to said intravenous infusion assembly and to said heat exchange assembly; wherein said controller includes the use of a flow feedback algorithm comprising:

$$P = (T_{set} - T_0) C_s \frac{F}{\epsilon} - \alpha \dot{T}_2$$

where $T_{set}$ is the set point temperature, $T_0$ is the initial fluid temperature in °C., $C_s$ is the heat capacity of the IV solution, F is the IV fluid flow in (ml/sec), $\epsilon$ is the working efficiency of the heat exchanger, $\dot{T}_2$ is the time derivative of the final fluid temperature $T_2$, and $\alpha$ is an empirical damping coefficient; and (d) an energy source functionally associated with said controller and said heat exchange assembly.

2. The device of claim 1 in which the heat exchange assembly includes an insulating cover within the intravenous infusion assembly and which encases the heat exchange assembly.

3. The device of claim 1 wherein the heat exchange assembly is comprised of at least one uniform resistive heater.

4. The device of claim 1 wherein the heat exchange assembly is comprised of at least one tapered resistive heater.

5. The device of claim 1 wherein the heat exchange assembly is comprised of at least one exponentially tapered heater.

6. The device of claim 5 wherein the surface temperature of the heating element at maximum electrical current is designed to be an isotherm at a particular flow rate, initial fluid temperature, and air temperature.

7. The device of claim 2 wherein the heating element assembly includes a two-current isothermal warmer which comprises a uniform heating element and an exponentially tapered heating element.

8. The device of claim 7 wherein the surface temperature of the insulating cover for said heating elements, at maximum electrical current, is an isotherm at a particular flow rate, initial fluid temperature, and air temperature.

9. The device of claim 5 wherein said heat exchange assembly comprises two or more exponentially tapered heater elements in series.

10. The device of claim 9 wherein the surface temperature of the insulating cover for said heating elements, at maximum electrical current, is an isotherm at a particular flow rate, initial fluid temperature, and air temperature.

11. The device of claim 5 wherein said heat exchange assembly comprises at least one uniform heater element and at least one exponentially tapered heater elements in series.

12. The device of claim 11 wherein the surface temperature of the insulating cover for said heating elements, at maximum electrical current, is an isotherm at a particular flow rate, initial fluid temperature, and air temperature.

13. The device of claim 5 wherein said heat exchange assembly comprises two or more exponentially tapered heater elements in parallel.

14. The device of claim 13 wherein the surface temperature of the insulating cover for said heating elements, at maximum electrical current, is an isotherm at a particular flow rate, initial fluid temperature, and air temperature.

15. The device of claim 5 wherein said heat exchange assembly comprises at least one uniform heater element and at least one exponentially tapered heater elements in parallel.

16. The device of claim 15 wherein the surface temperature of the insulating cover for said heating elements, at maximum electrical current, is an isotherm at a particular flow rate, initial fluid temperature, and air temperature.

17. The device of claim 6 wherein said controller includes the use of a flow feedback algorithm comprising $$P = (T_{set} - T_0) C_s \frac{F}{\epsilon} - \alpha \dot{T}_2$$

where $T_{set}$ is the set point temperature, $T_0$ is the initial fluid temperature in °C., $C_s$ is the heat capacity of the IV solution, F is the IV fluid flow in (ml/sec), $\epsilon$ is the working efficiency of the heat exchanger, $\dot{T}_2$ is the time derivative of the final fluid temperature $T_2$, and $\alpha$ is an empirical damping coefficient.

18. The device of claim 6 wherein said heating elements are arranged in parallel.

19. The device of claim 8 wherein said controller includes the use of a flow feedback algorithm comprising where $T_{set}$ is the set point temperature, $T_0$ is the initial fluid temperature in °C., $C_s$ is the heat capacity of the IV solution, F is $$P = (T_{set} - T_0) C_s \frac{F}{\epsilon} - \alpha \dot{T}_2$$

the IV fluid flow in (ml/sec), $\epsilon$ is the working efficiency of the heat exchanger, $\dot{T}_2$ is the time derivative of the final fluid temperature $T_2$, and $\alpha$ is an empirical damping coefficient.

20. The device of claim 19 wherein:
(a) The electrical current through each heater element has a maximum allowable value defined by $I_1MAX$ and $I_2MAX$, respectively;
(b) The uniform heater element is energized fully ($I_1 = I_1MAX$) before the exponentially tapered heater is energized; and
(c) The tapered heater will not be energized below a particular flow rate.

21. The device of claim 10 wherein said controller includes the use of a flow feedback algorithm comprising $$P = (T_{set} - T_0) C_s \frac{F}{\epsilon} - \alpha \dot{T}_2$$

where $T_{set}$ is the set point temperature, $T_0$ is the initial fluid temperature in °C., $C_s$ is the heat capacity of the IV solution, F is the IV fluid flow in (ml/sec), $\epsilon$ is the working efficiency of the heat exchanger, $\dot{T}_2$ is the time derivative of the final fluid temperature $T_2$, and $\alpha$ is an empirical damping coefficient.

22. The device of claim 21 wherein:
(a) The electrical current through each heater element has a maximum allowable value defined by $I_1MAX$ and $I_2MAX$, respectively;

(b) The downstream, $I_2$, heater element is energized fully ($I_2=I_2MAX$) before the exponentially tapered heater is energized; and (c) The upstream, $I_1$, heater will not be energized below a particular flow rate.

23. The device of claim 20 wherein the device further comprises a plurality of said heat exchange assemblies removably mounted to a plurality of said intravenous infusion assemblies which are operated in parallel.

24. The device of claim 20 wherein the device further comprises a plurality of said heat exchange assemblies removably mounted to a plurality of said intravenous infusion assemblies which are operated in series.

25. The device of claim 22 wherein the device further comprises a plurality of said heat exchange assemblies removably mounted to a plurality of said intravenous infusion assemblies which are operated in parallel.

* * * * *